United States Patent

Milan et al.

[11] Patent Number: 5,948,766
[45] Date of Patent: Sep. 7, 1999

[54] USE OF TASTELESS, HYDROLYZED COLLAGEN AND AGENT CONTAINING THE SAME

[75] Inventors: Adam Milan, Prag, Czech Rep.; Bernd Eggersglüss, Heddesbach, Germany; Klaus Bräumer; Reinhard Schrieber, both of Eberbach, Germany

[73] Assignee: DGF Stoess AG, Eberbach, Germany

[21] Appl. No.: 08/793,252

[22] PCT Filed: Aug. 19, 1995

[86] PCT No.: PCT/EP95/03304

§ 371 Date: Apr. 25, 1997

§ 102(e) Date: Apr. 25, 1997

[87] PCT Pub. No.: WO96/05851

PCT Pub. Date: Feb. 29, 1996

[30] Foreign Application Priority Data

Aug. 23, 1994 [DE] Germany ............... 44 29 842

[51] Int. Cl.⁶ ............ A61K 38/01; A61K 38/23
[52] U.S. Cl. ............. 514/21; 514/2; 514/801; 514/808; 514/825; 424/678; 424/682; 530/356; 530/840
[58] Field of Search ............ 530/356, 840; 514/21, 2, 801, 808, 825; 424/678, 682

[56] References Cited

U.S. PATENT DOCUMENTS 4,804,745 2/1989 Koepff et al. ............... 530/356
4,919,931 4/1990 Goldner ....................... 424/95
5,641,747 6/1997 Popoff et al. ................. 514/12

FOREIGN PATENT DOCUMENTS

| 1 077 630 | 10/1993 | China . |
| 0 254 289 | 1/1988 | European Pat. Off. . |
| 494 250 | 9/1970 | Switzerland . |
| 1227534 | 4/1971 | United Kingdom . |

OTHER PUBLICATIONS

CAS Registry No. 9000–70–8, Ossein, 1997.

Lugli, et al., Effect of Ossein Hydroxyapatie Compound (Ossan) on Back Pain in the Elderly. Results of a Placebo–ontrolled Trial. Clin.Trials J., vol. 27, No. 3, pp. 141–148, 1990.

Dambacher, et al., The Drug Treatment of Osteopososis—The Present Position, Schweiz. Apoth. Ztg., vol. 125, No. 13, pp. 372–375, 1987.

*Primary Examiner*—Cecilia J. Tsang
*Attorney, Agent, or Firm*—Jacobson, Price, Holman & Stern, PLLC

[57] ABSTRACT

Tasteless, hydrolyzed collagen from gelatin, gelatin or animal collagenic connective tissue having an average molecular weight of from 1 to 40 kD for the preparation of agents for the treatment of osteoporosis. It may be combined with conventional agents for combatting osteoporosis, such as calcitonin, calcium salts, and/or progesterone.

8 Claims, 6 Drawing Sheets

USE OF TASTELESS, HYDROLYZED COLLAGEN AND AGENT CONTAINING THE SAME

The present invention pertains to the use of tasteless, hydrolyzed collagen from gelatin, gelatin or animal collagenic connective tissue having an average molecular weight of from 1 to 40 kD, and to agents containing the same.

From EP-B-0 254 289, there are known agents for the treatment of arthroses containing tasteless, enzymatically hydrolyzed collagen from animal skin, animal bones, sufficiently purified connective tissue, or gelatin, having an average molecular weight of from 10 to 80 kD.

DE-A-36 26 414 describes a preparation for stimulating chondrocytes and osteoblasts (ossein/hydroxyapatite complex), as well as methods for the preparation thereof and medicaments containing the same. The preparation is obtained by purifying and grinding bones and therefore contains native collagen. The most important component of the preparation, however, is the ossein/hydroxyapatite complex with its high calcium and phosphate contents.

JP-A-05 05 1400 describes the formation of a preparation from cell cultures of rabbit cartilage. The collagen has a molecular weight of 60 kD and consists of type II.

GB-PS-1 227 534 describes the preparation of a collagen hydrolysate by alkaline or acid pressure hydrolysis. In addition to degraded collagen, this preparation contains from 4 to 15% of free amino acids. The starting material is not specified. This preparation is preferably intended for use with calcium salts and is said to enable increased calcium supply.

Osteoporosis is defined as the clinical manifestation of bone atrophy. This means a reduction of the bone mass for a given volume. To date, more than 20 causes have been known for the occurrence of osteoporosis. The most frequent forms are postmenopausal and senile osteoporoses. From the beginning of the fifth decade of life, the whole bone mass begins to decrease.

This is due to the fact that from this point, there is more bone mass destroyed than formed. Osteoporosis is the most wide-spread metabolic disease of bone which increases with age, predominantly with females.

Three to five years after the menopause, there is usually a sudden occurrence of loss of bone mass. This is manifested by the occurrence of fractures of the spiny column, fractures of the femoral neck and of the forearm. Mostly, at the point of first occurrence of a fracture, only about 50% of the original bone mass are retained.

Early diagnosis of osteoporosis is a great problem since in the normal X-ray picture, it only shows after a loss of at least 30% of the bone mass.

Osteoporotic changes are also associated with a reduction of the number of collagen fibers of the bone. The degradation products of this collagen catabolism can be increasedly detected in the urine.

From a molecular point of view, the bone has a unique collagen composition. It is the only tissue in which type I collagen is not associated with type III collagen. The collagen structures are stabilized by cross-links which are effected by two amino acid residues of lysine and hydroxylysine.

Several other cross-linking possibilities have been described. Fujimoto (Biochem. Biophys. Res. Commun. 1977; 76: 1124–1129) describes cross-linking elements derived from three lysine or hydroxylysine residues, i.e. pyridinoline (PD) and deoxypyridinoline (DPD).

Their occurrence is connective tissue specific, but neither limited to a particular tissue type nor to a particular collagen type. It is known that collagens of types I, II, III, IX, X and XI can form this kind of cross-links.

These cross-links are not degraded by the body and are excreted with the urine. Therefore, their content in the urine is a good indicator of collagen degradation.

Agents for the treatment of osteoporosis include calcitonin, calcium salts, such as calcium fluoride and calcium bis(phosphonates), as well as progesterone.

It is the object of the present invention to provide further agents for the treatment of osteoporosis. This object has now been achieved by the use of tasteless, hydrolyzed collagen from gelatin, gelatin or animal collagenic connective tissue having an average molecular weight of from 1 to 40 kD for the preparation of agents for the treatment of osteoporosis. The collagen is preferably derived from skin and therefore contains collagen types I and III as the main components. Gelatin itself mostly has an average molecular weight of from 100 to 500 kD. The molecular weights are determined by HPLC with non-globular standard peptides from collagen. These are mostly obtained by cyanogen bromide degradation. The values of the molecular weights in EP-B-0 254 289 had still been determined with globular standard proteins and therefore are significantly higher than those measured today with HPLC and non-globular standard proteins.

Figure 1:
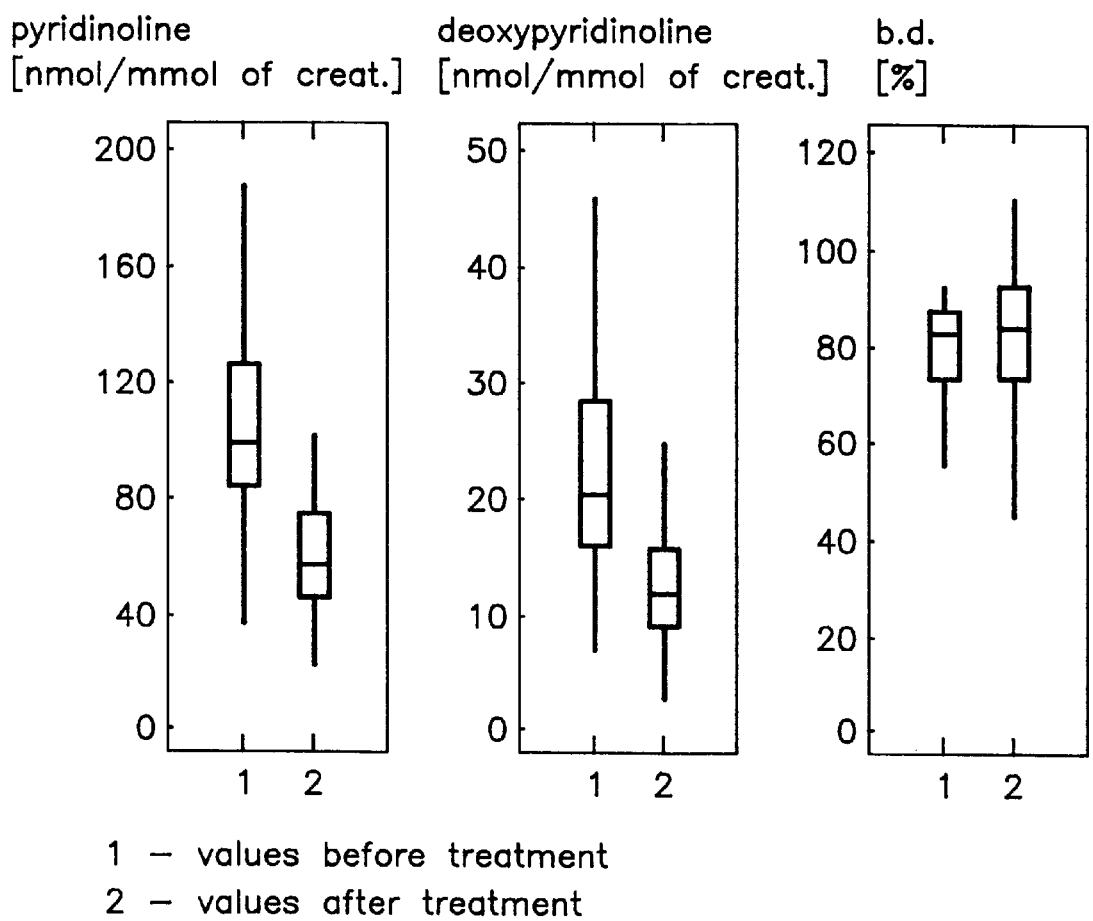
FIG. 1 diagrams results of a clinical study on the influence of collagen hydrolysate-calcitonin therapy on urine excretion of pyridinoline, deoxypyridinoline, and bone mass density.

The agents prepared according to the invention are preferably formulated as pastes, syrups, solutions, granules, compressed formulations or instantized powders. These agents can additionally be added with flavouring agents, sweeteners, minerals and/or vitamins.

They are preferably packaged in dosage forms containing from 0.5 to 12 g of hydrolyzed collagen.

Finally, it has been found that these agents are particularly effective if they are additionally added with the known agents for the treatment of osteoporosis, such as calcitonin, the above mentioned calcium salts, and/or progesterone.

Thus, another subject matter of the present invention is an agent for the treatment of osteoporosis containing tasteless, hydrolyzed collagen from gelatin, gelatin or animal collagenic connective tissue having an average molecular weight of from 1 to 40 kD, and in addition calcitonin, calcium salts, and/or progesterone.

Hydrolyzed collagen can be obtained by the usual known methods, and gelatin can be obtained by the method as described in "The Science and Technology of Gelatine", A. G. Ward and A. Courts, Academic Press, 1977. The preparation of low molecular weight, cold water soluble collagen hydrolysates is described in "Enzymatic Hydrolysis of Food Proteins", Jens Adler-Nielsen, Elsevier Applied Science Publishers, London and New York. Enzymatically hydrolyzed collagen from skin is preferably employed.

In a clinical study with a preferred preparation (Gelitasol®, MW 3.5 kD), it was now established that hydrolyzed collagen is also effective against osteoporosis. The object of this study has been to establish the effect which a diet rich in collagen hydrolysate has on bone metabolism, i.e. whether a diet rich in collagen hydrolysate together with calcitonin causes a higher bone collagen metabolism than the administration of calcitonin alone.

The results of this treatment were evaluated by the clinical findings, X-ray pictures, osteometry and chemical examinations including the determination of pyridinoline and deoxypyridinoline in urine.

The following double-blind study was performed:

The subjects were females aged more than 40 years suffering from postmenopausal osteoporosis in which the bone mass was less than 80% according to X-ray results and densitometric determinations.

The following exclusion criterions were used:

- severe joint and discogenic diseases, whether of inflammatory, metabolic or degenerative origin;
- chronic systemic infectious diseases;
- functional disorders of kidney or liver;
- intensive osteoporosis therapy;
- former (1 year before begin of study) or current corticosteroid therapy;
- malign diseases.

Patients 121 females after menopause which were known from X-ray diagnosis to clearly suffer from osteoporosis were selected for this study.

27 of these patients prematurely discontinued the study, mainly because of calcitonin incompatibility (nausea, vomiting, hot flushes).

Therapy

The remaining 94 patients were divided into two randomized groups, and by accident, 47 in each group were left for the total double-blind study.

One group received a diet rich in collagen hydrolysate and was additionally treated with calcitonin. The other group was only treated with calcitonin, and lactose as a placebo. The calcitonin treatment was performed twice a week with 100 U i.m. The study was performed for a period of 24 weeks.

The anthropometric and specific data of the patients can be seen from table 1, and the risk factors can be seen from table 2.

TABLE 1

Basic data of the subjects

|  | calcitonin + collagen hydrolysate | calcitonin | total |
|---|---|---|---|
| number of patients | 47 | 47 | 94 |
| age av. | 61.43 | 58.94 | 60.18 |
| S. | 8.18 | 8.68 | 8.53 |
| height |  |  |  |
| av. | 163.09 | 163.11 | 163.10 |
| S. | 5.41 | 7.11 | 6.32 |
| weight |  |  |  |
| av. | 66.17 | 70.64 | 68.40 |
| S. | 10.90 | 15.15 | 13.38 |
| pregnancies |  |  |  |
| av. | 1.91 | 1.94 | 1.93 |
| S. | 1.15 | 1.10 | 1.12 |
| menstruation |  |  |  |
| from av. | 13.55 | 13.54 | 13.54 |
| S. | 1.38 | 1.65 | 1.53 |
| to av. | 48.74 | 47.17 | 47.96 |
| S. | 4.87 | 5.81 | 5.42 |

TABLE 2

Frequency of risk factors in each of the groups

|  | calcitonin + collagen hydrolysate | calcitonin | total |
|---|---|---|---|
| number of patients | 47 | 47 | 94 |
| restricted movement | 30 | 29 | 59 |
| abuse of alcohol | 1 | 1 | 2 |
| abuse of nicotine | 10 | 9 | 19 |
| abuse of coffeine | 7 | 5 | 12 |
| chronic renal disease | 0 | 0 | 0 |
| gastrointestinal trouble | 0 | 0 | 0 |
| hyperthyreosis | 3 | 8 | 11 |
| hyperparathyreosis | 0 | 0 | 0 |
| corticosteroids | 1 | 0 | 1 |
| urolithiasis | 2 | 2 | 4 |
| painful menstruation | 7 | 11 | 18 |
| high-performance sports | 7 | 6 | 11 |
| leisure-time sports | 25 | 16 | 41 |

Examinations

The following examinations were performed both prior to the beginning and after the end of the study, and with 61 patients three months after the end of the therapy:

- bone density of the right forearm by single photon absorptiometry measurements (with most of the patients);
- X-ray examination of the right forearm, the lumbar vertebrae, or other sensitive parts of the spinal column;
- serum analyses;
- determination of pyridinoline and deoxypyridinoline in the urine;
- determination of hydroxyproline in the urine.

Results

The final evaluation of therapeutic effectiveness was performed in a three step rating in terms of the subjective condition of the patients. The measuring values obtained were evaluated statistically with the aid of STATGRAPHICS soft ware (STST Inc. Rockville, Md., U.S.A.). The influence of non-linear variables was calculated by means of a one-sided variance test. Significant differences were checked by the last significance intervals range test.

In the X-ray picture and in the densitometric measurements, no differences could be found, which is in accordance with the publication by Villareal et al. (osteoporosis Int. 1992; 2: 70–73). The laboratory values (with the exception of UPD/creatinin and U hydroxyproline/creatinin) were normal at the beginning of the study and remained unchanged during the treatment, see table 3.

TABLE 3

Urine values

|  |  | calcitonin + collagen hydrolysate | | calcitonin | | total | |
| --- | --- | --- | --- | --- | --- | --- | --- |
| months |  | 0 | 6 | 0 | 6 | 0 | 6 |
| number of patients |  | 47 | | 47 | | 94 | |
| BSR, 1 h | av. | 18.6 | 15.3 | 18.7 | 17.4 | 18.7 | 18.7 |
| serum calcium | av. | 2.37 | 2.35 | 2.38 | 2.33 | 2.38 | 2.34 |
| (mmol/l) | S. | 0.39 | 0.24 | 0.31 | 0.29 | 0.36 | 0.27 |
| phosphorus in serum | av. | 1.18 | 1.29 | 1.17 | 1.25 | 1.18 | 1.27 |
| (mmol/l) | S. | 0.24 | 0.35 | 0.18 | 0.35 | 0.21 | 0.35 |
| alkaline phosphatase | av. | 1.42 | 1.40 | 1.25 | 1.32 | 1.33 | 1.37 |
| in serum (ukat/l) | S. | 1.24 | 0.69 | 0.45 | 0.65 | 0.93 | 0.68 |
| acid phosphatase | av. | 0.21 | 0.18 | 0.18 | 0.18 | 0.19 | 0.18 |
| in serum (ukat/l) | S. | 0.13 | 0.17 | 0.05 | 0.21 | 0.10 | 0.19 |
| calcium in urine | av. | 0.38 | 0.51 | 0.51 | 0.55 | 0.44 | 0.53 |
| (mmol/mmol of creat.) | S. | 0.35 | 0.39 | 0.95 | 0.92 | 0.72 | 0.70 |
| phosphate in urine | av. | 2.47 | 2.40 | 2.97 | 2.75 | 2.72 | 2.57 |
| (mmol/mmol of creat.) | S. | 1.85 | 1.79 | 2.71 | 2.78 | 2.34 | 2.32 |

The UPD/creatinin and UDPD/creatinin excretions decreased from an initial average of 109.6 to 61.67 nmol/mmol. However, there is a significant difference between the two examination groups. In the group treated with collagen hydrolysate and calcitonin, the initial values of UPD/creatinin and UDPD/creatinin were, respectively, 114.98 and 23.51 nmol/mmol which decreased to 58.62 and 11.60 nmol/mmol, respectively, after the study.

In the group without collagen hydrolysate, these values decreased to a very much smaller extent, namely UPD/creatinin from 104.14 to 22.22 nmol/mmol, and UDPD/creatinin from 64.73 to 16.73 nmol/mmol, see table 4.

As compared to healthy adults, the excretion of the collagen degradation products was significantly increased in both groups, see table 5.

TABLE 4

Urine values of collagen degradation products

|  |  | calcitonin + collagen hydrolysate | | calcitonin | | total | |
| --- | --- | --- | --- | --- | --- | --- | --- |
| months |  | 0 | 6 | 0 | 6 | 0 | 6 |
| number of patients |  | 47 | | 47 | | 94 | |
| hydroxyproline | av. | 18.8 | 18.9 | 18.0 | 18.1 | 18.4 | 18.5 |
| ($\mu$mol/mmol of cr.) | S. | 10.2 | 13.9 | 12.3 | 9.5 | 11.3 | 12.0 |
| pyridinoline | av. | 115.0 | 58.6 | 104.1 | 64.7 | 109.6 | 61.7 |
| (nmol/mmol of cr.) | S. | 65.4 | 21.3 | 37.9 | 21.6 | 53.7 | 21.6 |
| deoxypyridinoline | av. | 23.6 | 11.6 | 22.2 | 16.7 | 22.8 | 14.2 |
| (nmol/mmol of cr.) | S. | 10.4 | 4.9 | 11.4 | 27.9 | 10.9 | 20.2 |
| bone density | av. | 76.1 | 79.5 | 77.0 | 79.5 | 76.6 | 79.5 |
| (%) | S. | 10.0 | 13.9 | 11.2 | 14.3 | 10.7 | 14.1 |

TABLE 5

Urine values of collagen degradation products control group

|  | control group |
| --- | --- |
| hydroxyproline | |
| ($\mu$mol/mmol of creatinin) | |
| av. | 15.7 |
| S. | 8.2 |
| pyridinoline | |
| (nmol/mmol of creatinin) | |
| av. | 41.6 |
| S. | 10.6 |
| deoxypyridinoline | |
| (nmol/mmol of creatinin) | |
| av. | 8.1 |
| S. | 2.8 |

The relative changes of UPD/creatinin, UDPD/creatinin and bone density (b.d.) are represented in FIG. 1.

Figure 2:
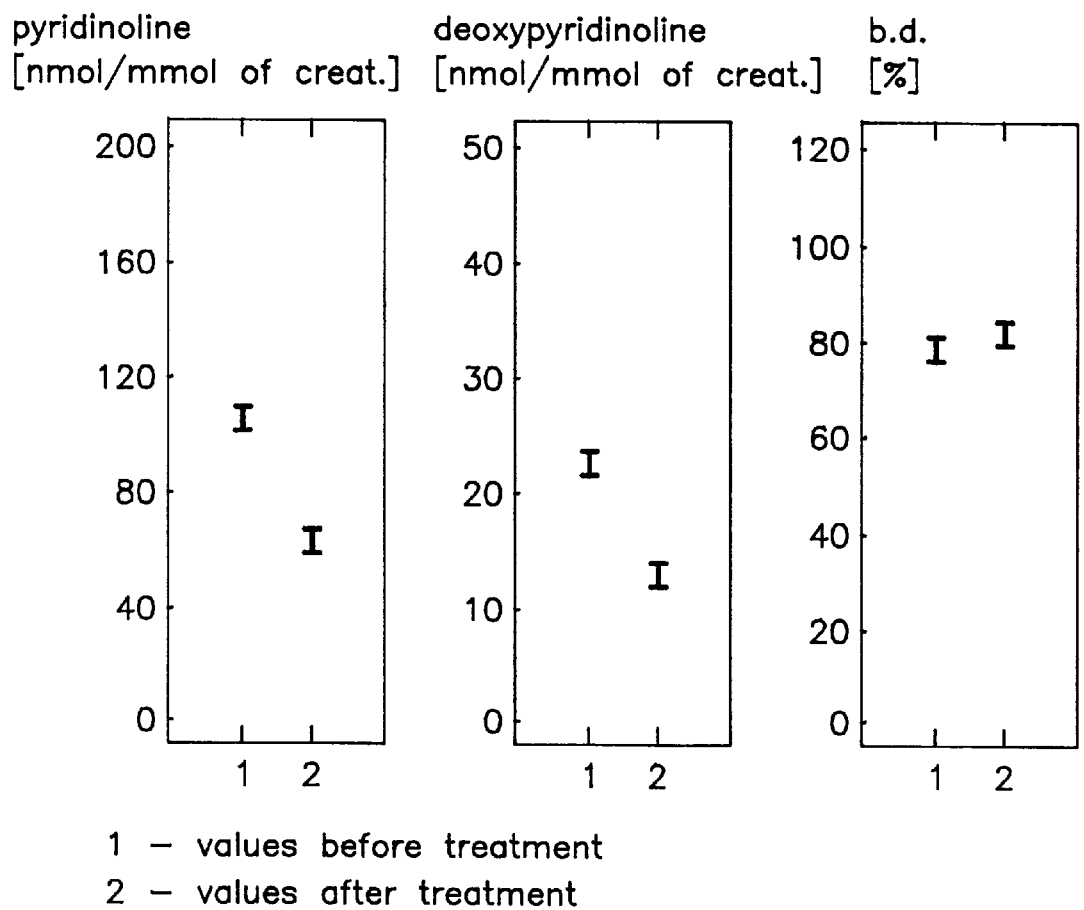
FIG. 2 diagrams the statistical significant (about 95% between the values before treatment and the values after treatment shown in FIG. 1.

FIG. 2 shows the statistical significance of the decrease of the two biochemical markers in osteoporotic patients as compared to the initial values. The differences are significant (5% level). On the other hand, no increase of bone mass density could be established.

Figure 3:
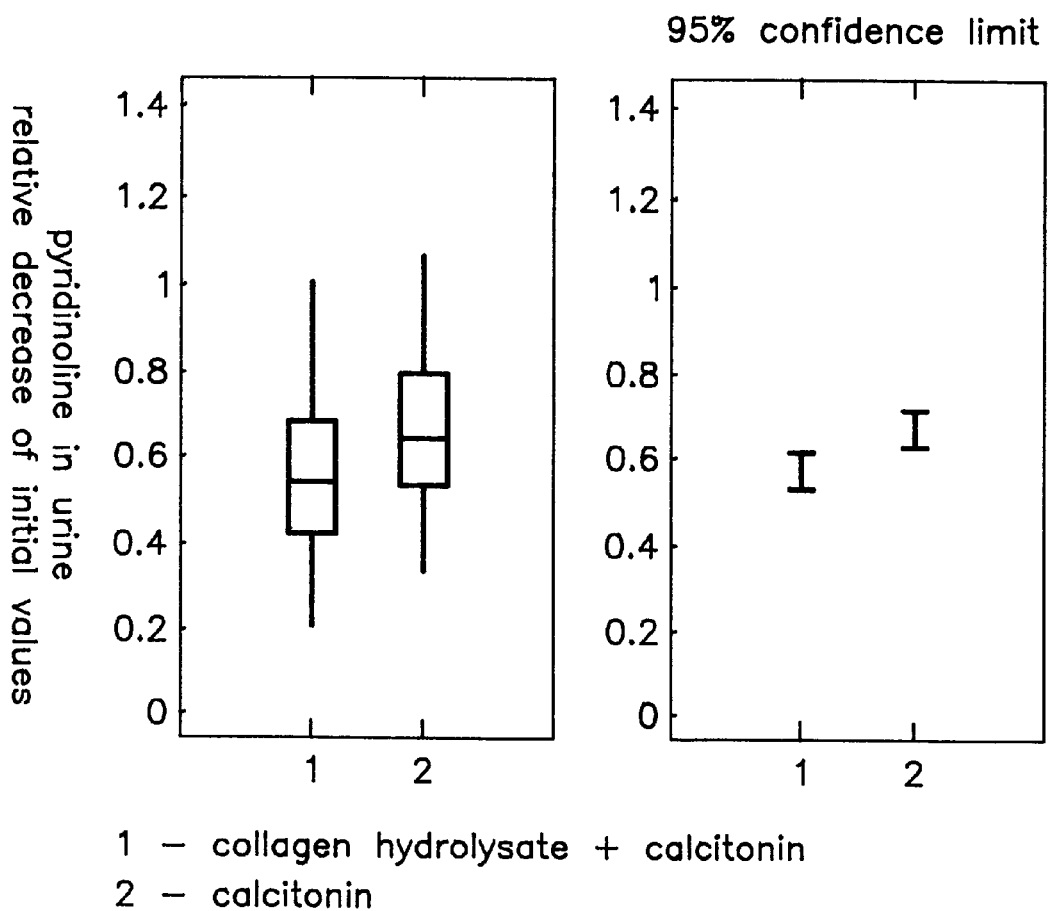
FIGS. 3 and 4 diagram the imperative results between therapy using calcitonin, alone, and calcitonin plus collagen hydrolysate.
Figure 4:
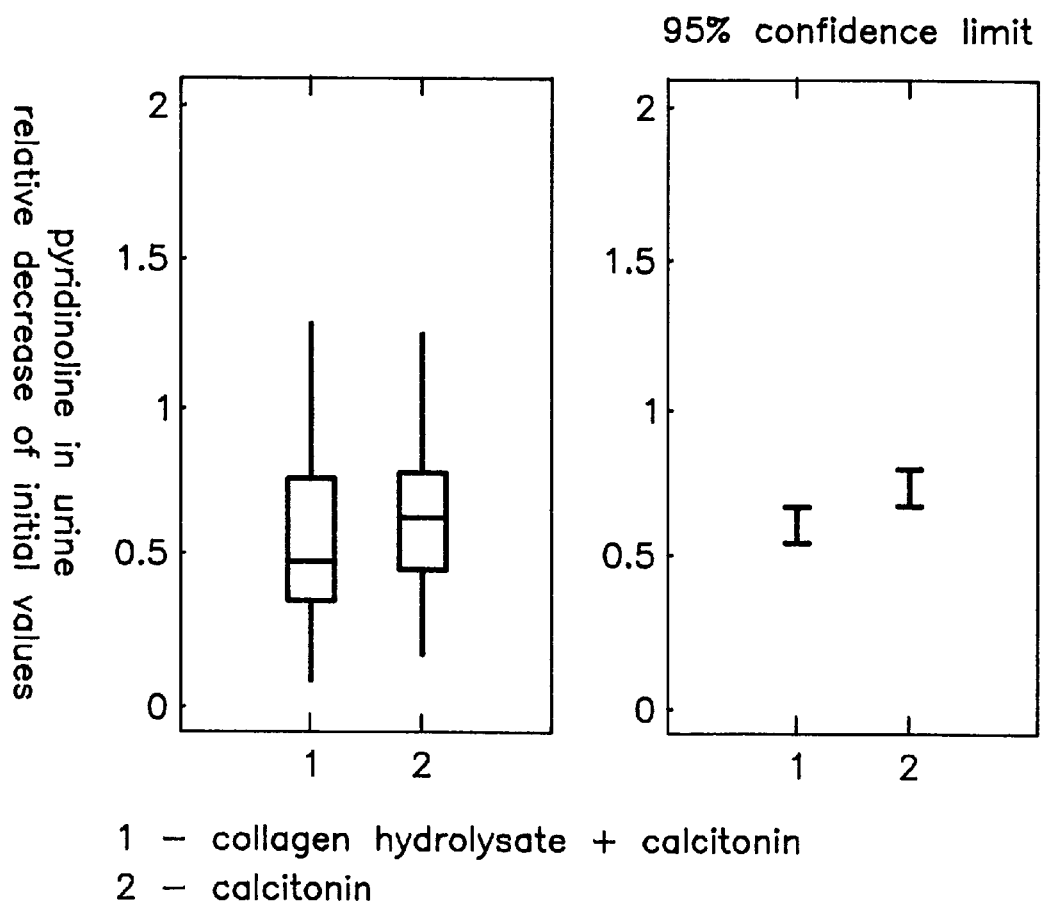
Figure 5:
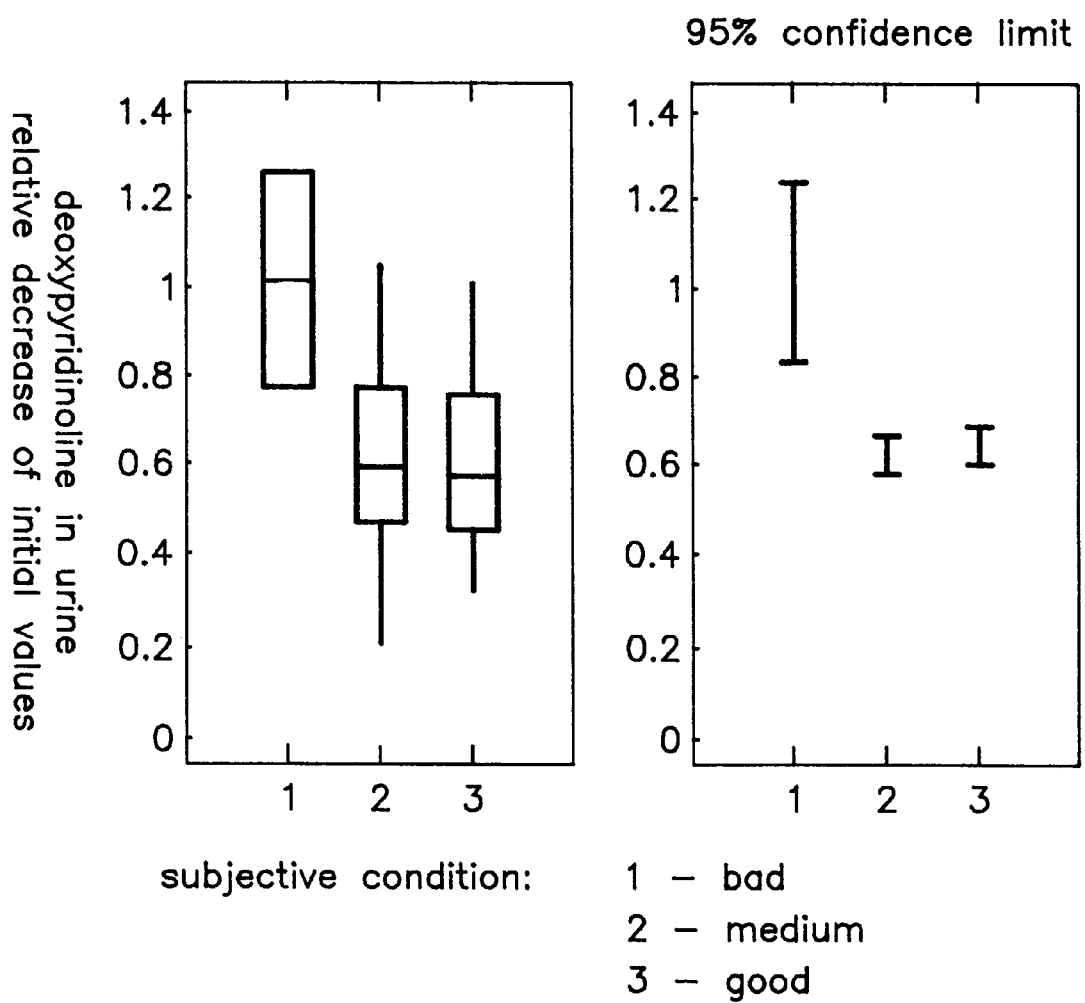
FIG. 5 diagrams comparison between the relative decrease (from determined initial values) of pyridinoline excretion in urine, on the one hand, and a subjective evaluation, on the other, following therapy.
Figure 6:
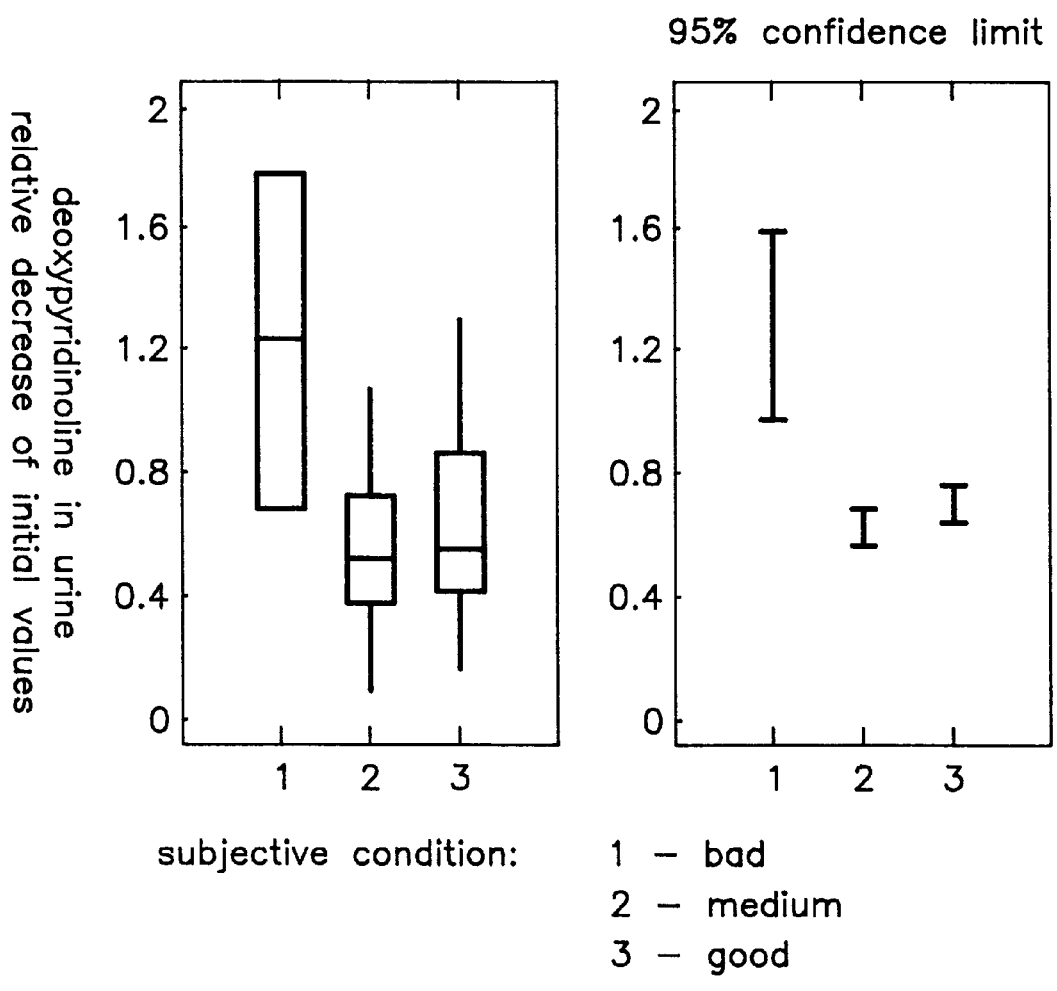
FIG. 6 diagrams the comparison between the relative decrease (from initial values) of deoxypyridinoline excretion in urine on the one hand, and a subjective evaluation, on the other, following therapy.

FIGS. 3 and 4 show that the therapy with collagen hydrolysate a better result than that with calcitonin alone.

In patients examined three months after the end of the therapy, the pyridinoline and deoxypyridinoline excretions were still reduced as compared to the initial values. In the group treated with collagen hydrolysate, this was more pronounced than in the group which had received calcitonin only, see table 6.

The changes of the pyridinoline/creatinin values in the patients with collagen hydrolysate were 53.05% after the therapy and decreased to 49.27% until three months later.

In patients treated with calcitonin alone, the corresponding decreased from 67.95 to 67.51%.

The evaluation of the subjective statements of the patients concerning the effectiveness of the therapy had the result that those treated with collagen hydrolysate stated a greater improvement of their conditions than those treated with calcitonin alone. It is remarkable that the improvement of the subjective symptoms correlates with the decrease of the pyridinoline/creatinin and deoxypyridinoline/creatinin values (see diagrams 5 and 6).

TABLE 6

|  | calcitonin + collagen hydrolysate | | | calcitonin | | | total | | |
| --- | --- | --- | --- | --- | --- | --- | --- | --- | --- |
| months | 0 | 6 | 9 | 0 | 6 | 9 | 0 | 6 | 9 |
| number of patients | | 30 | | | 30 | | | 60 | |
| hydroxyproline | 17.7 | 21.1 | 12.8 | 18.1 | 17.1 | 14.0 | 17.9 | 19.1 | 13.4 |
| (μmol/mmol of creat.) | 9.6 | 16.0 | 6.1 | 14.4 | 8.0 | 6.2 | 12.2 | 12.7 | 6.2 |
| pyridinoline | 125.4 | 59.9 | 57.0 | 108.9 | 69.2 | 66.2 | 117.0 | 64.9 | 61.7 |
| (nmol/mmol of creat.) | 76.8 | 20.9 | 18.7 | 39.9 | 23.1 | 26.4 | 61.5 | 22.5 | 23.4 |
| deoxypyridinoline | 24.7 | 11.6 | 11.9 | 24.8 | 19.2 | 14.4 | 24.7 | 15.4 | 13.6 |
| (nmol/mmol of creat.) | 11.1 | 5.1 | 4.9 | 12.6 | 34.0 | 6.7 | 11.9 | 24.8 | 6.0 |
| (%) bone density | 77.3 | 81.2 | 80.7 | 79.3 | 82.3 | 81.9 | 78.3 | 81.8 | 81.3 |
| | 8.2 | 12.1 | 11.2 | 9.9 | 13.4 | 14.3 | 9.2 | 12.8 | 12.8 |

Conclusions:

The collagen of bone exclusively consists of type I which contains an extraordinary high fraction of pyridinoline in the form of cross-links, more than occurs in other connective tissues. Since the bone is the only tissue to renew its structural elements to a high extent (Kamel et al., J. chromatogr. 1992; 574: 255–260), it is assumed that the pyridinoline which is excreted in the urine is mainly derived from bone. This assumption is supported by the molar ratio of pyridinoline to deoxypyridinoline in urine which as a rule corresponds to that of the bone.

The hydroxyproline-to-creatinin ratio in the urine has proven to be unsuited for monitoring the bone metabolism since it is too much superimposed by the degradation of the collagen of other tissues and also by the collagen hydrolysate supplied.

It is known that the treatment of osteoporosis patients with calcitonin reduces the further bone loss, but there has been no indication to date that calcitonin therapy increases the bone density, except in long-term treatment. Further, calcitonin has an analgetic effect which must be considered separately from the effect on the bone, however. It is known that only a long-term treatment with calcitonin increases the bone density. On the other hand, gelatin stimulates the cell proliferation in vitro, and a positive effect of a diet rich in collagen hydrolysate has been observed in patients suffering from osteoarthrosis. Moreover, an improved wound healing, a better general well-being, and a reduction of backache has been established in these patients. As a result of these studies, it can be noted that the therapy of osteoporosis with diet rich in collagen hydrolysate is probably due to metabolic influences. Further, it is sure that a therapy with collagen hydrolysate and calcitonin exhibits stronger positive effects on bone metabolism than a treatment with calcitonin alone. This could still be observed three months after the therapies.

What is claimed is:

1. A method of treating osteoporosis comprising administering to a patient in need thereof a composition comprising tasteless, enzymatically hydrolyzed collagen from gelatin or animal collagenic connective tissue having an average molecular weight of from 1 to 40 kD, as determined by HPLC with non-globular standard peptides from collagen.

2. The method of claim 1 wherein said composition is formulated as a paste, a syrup, a solution, granules, a compressed formulation, or instantized powder.

3. The method of claim 1 wherein said composition further comprises flavoring agents, sweeteners, minerals and/or vitamins.

4. The method of claim 1, wherein the amount of the enzymatically hydrolyzed collagen is 0.5–12 g.

5. The method of claim 1 wherein the composition further comprises calcitonin, calcium salts, and/or progesterone.

6. A composition for treating osteoporosis comprising tasteless, enzymatically hydrolyzed collagen from gelatin or animal collagenic connective tissue having an average molecular weight of from 1 to 40 kD, as determined by HPLC with non-globular standard peptides from collagen, in combination with calcitonin, calcium salts, and/or progesterone.

7. The composition of claim 6 comprising 0.5–12 g of the enzymatically hydrolyzed collagen.

8. The composition of claim 6 packaged in a dosage form comprising 0.5–12 g of the enzymatically hydrolyzed collagen.

* * * * *